US00PP35300P2

(12) United States Plant Patent
Chaussard

(10) Patent No.: US PP35,300 P2
(45) Date of Patent: Aug. 8, 2023

(54) ***HIBISCUS* PLANT NAMED 'MINPAPAN1'**

(50) Latin Name: ***Hibiscus syriacus* x *paramutabilis* hybrid**
Varietal Denomination: MINPAPAN1

(71) Applicant: Hortival Diffusion SAS, Beaufort en Valee (FR)

(72) Inventor: Pierre Chaussard, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 18/077,429

(22) Filed: Dec. 8, 2022

(51) Int. Cl.

| | |
|---|---|
| ***A01H 5/00*** | (2018.01) |
| ***A01H 6/60*** | (2018.01) |
| ***A01H 5/02*** | (2018.01) |

(52) U.S. Cl.
USPC ..... Plt./257
CPC ..... *A01H 6/608* (2018.05); *A01H 5/02* (2013.01)

(58) Field of Classification Search
USPC ..... Plt./226, 257
See application file for complete search history.

(56) References Cited

U.S. PATENT DOCUMENTS

PP31,587 P2 * 3/2020 Hansen ..... A01H 5/02 Plt./257

* cited by examiner

*Primary Examiner* — Karen M Redden
(74) *Attorney, Agent, or Firm* — Cassandra Bright

(57) ABSTRACT

A new and distinct cultivar of *Hibiscus* plant named 'MINPAPAN1' is disclosed, characterized by lavender cup form flowers with a red eye extended by long lines. Leaves are green with large marginal light green variegation which comes and goes through the season. The new variety is a *Hibiscus*, typically produced as an ornamental plant.

3 Drawing Sheets

Latin name of the genus and species: *Hibiscus syriacus* x *paramutabilis* hybrid.

Variety denomination: 'MINPAPAN1'.

BACKGROUND OF THE INVENTION

The new *Hibiscus* cultivar is a product of a planned breeding program by the inventor with the objective of producing novel combinations of flowers and foliage. The seed parent is the unpatented variety *Hibiscus syriacus* 'Marina'. The pollen parent is the unpatented variety *Hibiscus paramutabilis* '7966'. The crossing resulting in this new cultivar was made in 2008 at a nursery in La Menitre, France.

The new cultivar was found and selected in September 2009 at the same nursery in La Menitre, France. Asexual reproduction of the new cultivar 'MINPAPAN1' was first performed in March 2012 by softwood cuttings. Subsequent propagation has shown that the unique features of this cultivar are stable and reproduced true to type in successive generations.

Date of first sale was Jun. 21, 2022, occurring in Grand Haven, Mich. This sale was made directly by the inventor or one who obtained the claimed invention directly or indirectly from the inventor. This sale and all public disclosures made between Jun. 21, 2022, and the filing of this application fall within the exception allowed under 102(b)(1).

SUMMARY OF THE INVENTION

The cultivar 'MINPAPAN1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINPAPAN1'. These characteristics in combination distinguish 'MINPAPAN1' as a new and distinct *Hibiscus* cultivar:

1. *Hibiscus sysriacus* x *paramutabilis* hybrid with variegated foliage without true reversion.
2. Green leaf with large marginal light green variegation which comes and goes through the season.
3. Lavender cup form flower with red eye extended by long lines.
4. Moderate growth rate.

PARENT COMPARISONS

Plants of the new cultivar 'MINPAPAN1' are similar to the seed parent in most horticultural characteristics. However, characteristics of the new cultivar differ in the following:

1. Foliage of the new variety is hybrid *parabmutabilis* form, with a large sized leaf. Foliage of the seed parent is *syriacus* form, with a medium sized leaf.
2. Leaves of the new variety are variegated, while leaves of the seed parent are not.
3. Flowers of the new variety are lavender with cup opening, while flowers of the seed parent are blue with flat opening.

Plants of the new cultivar 'MINPAPAN1' are similar to the pollen parent in most horticultural characteristics. However, characteristics of the new cultivar differ in the following:

1. Leaves of the new variety are variegated, while leaves of the pollen parent are not.
2. Flowers of the new variety are lavender, while flowers of the pollen parent are white.
3. Growth rate of the new variety is medium, while the growth rate of the pollen parent is vigorous.
4. Flowers of the new variety are medium sized, while flowers of the pollen parent are large.

COMMERCIAL COMPARISON

Plants of 'MINPAPAN1' are similar in some horticultural characteristics to the variety *Hibiscus syriacus* 'THEIS-SHSSTL', U.S. Plant Pat. No. 30,149. The new variety, however, differs in the following:

1. Leaves of the new variety have light green variegation, while leaves of this comparator have cream colored variegation.
2. Foliage of the new variety is hybrid *parabmutabilis* form, with a large sized leaf. Foliage of this comparator is *syriacus* form, with a medium sized leaf.
3. Flowers of the new variety are single and lavender colored, while flowers of this comparator are double and light pink colored.

BRIEF DESCRIPTION OF THE PHOTOGRAPHS

The accompanying photograph in FIG. 1 illustrates in full color typical plants of 'MINPAPAN1' grown outdoors at a commercial research nursery in Grand Haven, Mich. This plants are approximately 2 years old, grown in-ground, in a trial field.

Figure 1:
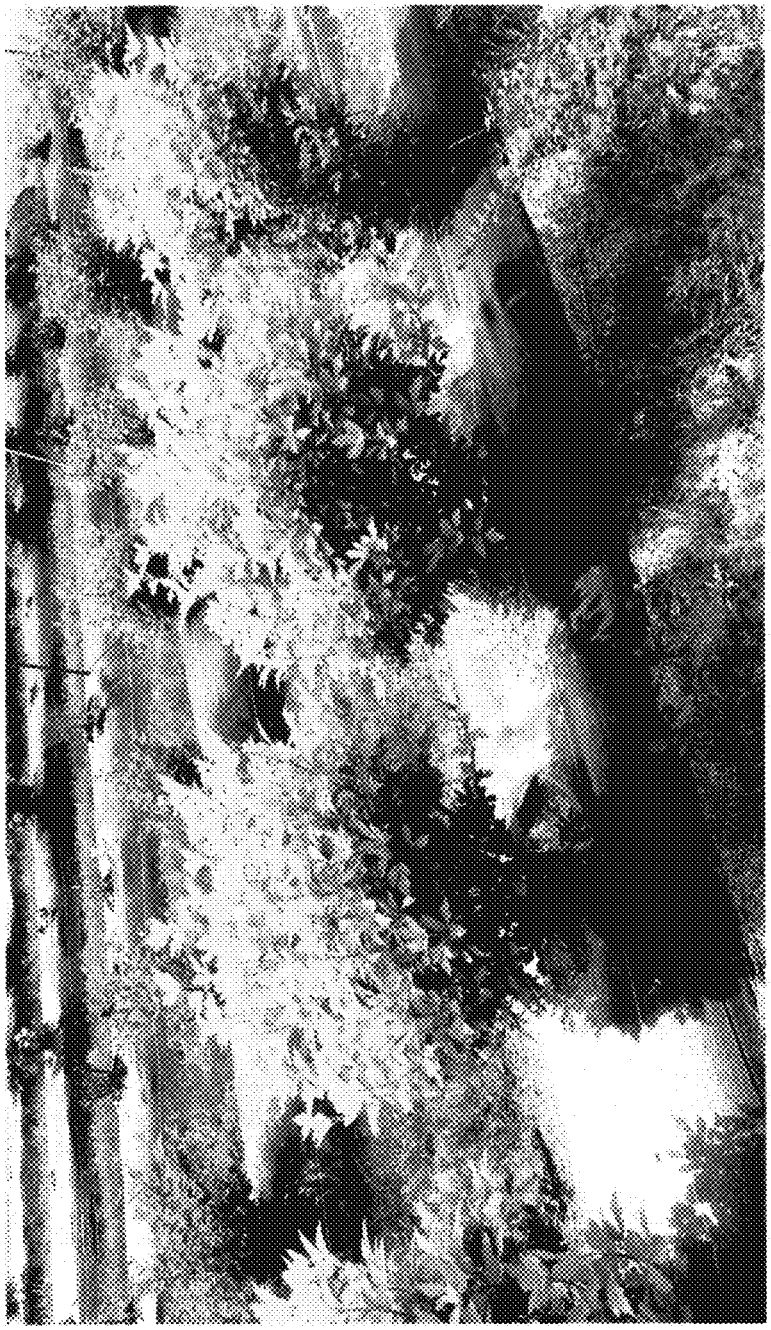
Figure 2:
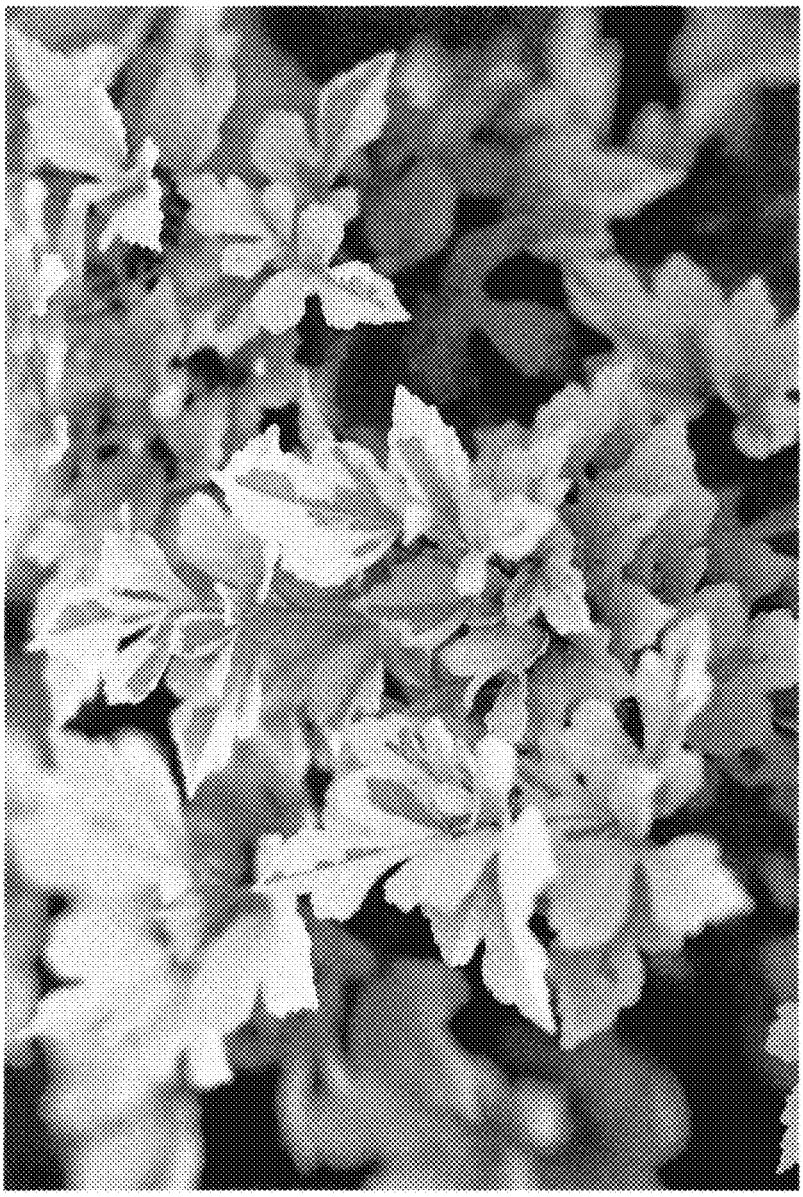
FIG. 2 illustrates a close-up view of the foliage.
Figure 3:
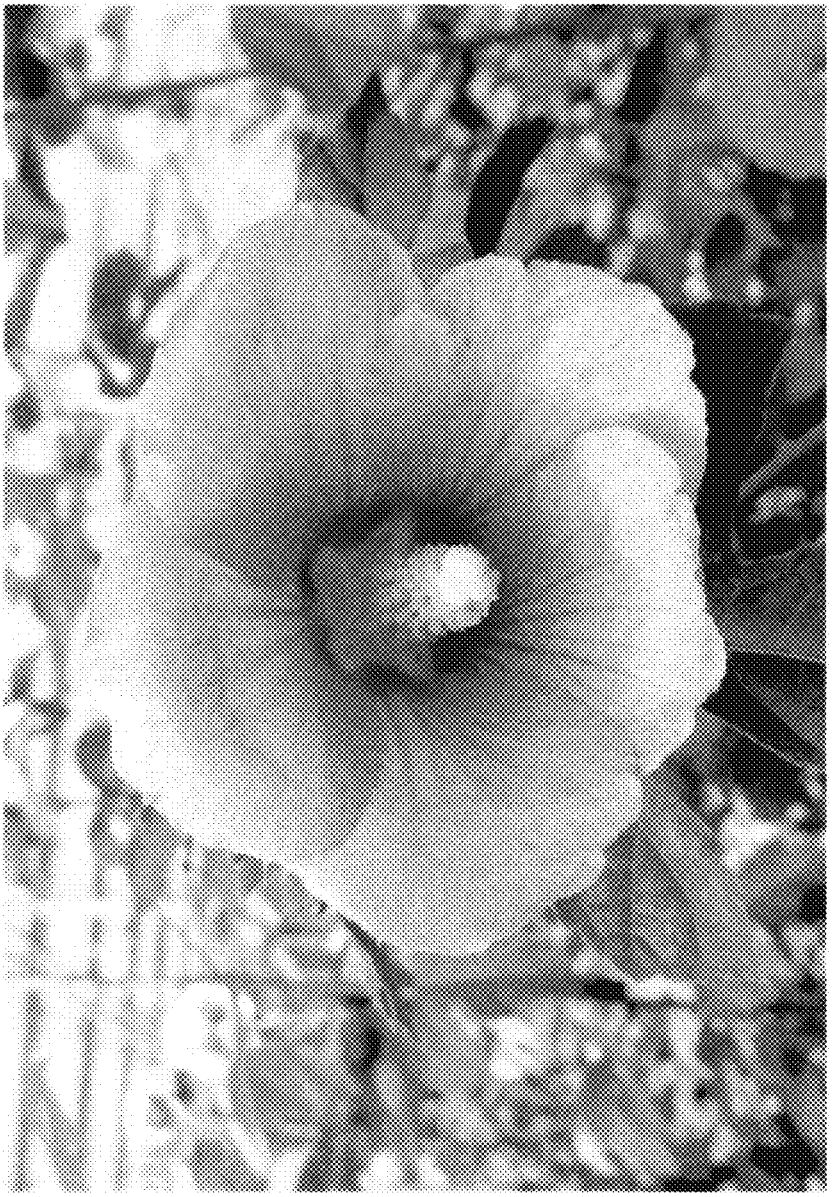
FIG. 3 illustrates a close-up view of a typical flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'MINPAPAN1' plant. This plant is approximately 3 years old, grown in a 3-gallon container. Temperatures ranged from 5° C. to 10° C. at night and 18° C. to 27° C. during the day. No artificial light, photoperiodic treatments were given to the plants. Measurements and numerical values represent averages of typical plant types.

Botanical classification: *Hibiscus syriacus* x *paramutabilis* hybrid 'MINPAPAN1'.

PROPAGATION

Time to initiate roots: 20 days s at 18° C.-27° C. during summer.

Time to produce a rooted plant: 90 days.

Root description: Fibrous, medium root thickness. Moderate branching and density. Tan/brown in color, not effectively measured with a color chart.

PLANT

Plant type: Perennial flowering shrub.

Age of plant described: 3 years old.

Growth habit: Upright.

Plant vigor: Moderate.

Height: 50 cm.

Plant spread: 40 cm.

Branching characteristics: Basal, pinching required.

Quantity of lateral branches: About 20.

Characteristics of primary lateral branches:

*Length*.—Average 35 cm.

*Diameter*.—3 to 5 mm.

*Shape*.—Rounded.

*Aspect*.—70-80° from horizontal, main basal stem 90°.

*Strength*.—Good, fairly rigid.

*Color*.—New growth: RHS Yellow-Green 144A with pubescence closest to Greyed-Green 196A. Mature growth: Near RHS Grey-Brown 199D.

*Pubescence*.—Yes, on newer growth only.

Internode length: Average 3 cm.

FOLIAGE

Leaf:

*Arrangement*.—Alternate, single.

*Average length*.—6 cm.

*Average width*.—6 cm.

*Shape of blade*.—Three-lobed; Oblanceolate center lobe with elliptic shaped lobes on either side.

*Apex*.—Acute to acuminate.

*Base*.—Obtuse.

*Margin*.—Lobed, serrate.

*Texture of top surface*.—Coriaceous.

*Texture of bottom surface*.—Rough-textured.

*Color*.—Young foliage upper side: RHS Yellow-Green 151B to N144A with blotchy Green 137B variegation, mostly near bottom half and center of leaf. Young foliage under side: RHS Yellow-Green 151B to N144A with blotchy Green 137B variegation, mostly near bottom half and center of leaf. Mature foliage upper side: RHS Green 137A-B. Mature foliage under side: RHS Green 137C.

*Venation*.—Type: Palmate. Venation color, upper side: RHS Green 137A-B. Venation color, under side: RHS Yellow-Green 144A.

*Petiole*.—Length: 2 cm. Diameter: 1 mm. Color: RHS Green 144A. Texture: Lightly pubescent.

*Other characteristics*.—New flush is variegated (see leaf colors as above) but fades to more of mature leaf color over time.

FLOWER

Natural flowering season: Mid to late summer.

Flower type and habit: Single flowers arranged at terminal ends of lateral branches in groups of 2 to 6, with some flowers emerging occasionally at leaf internodes.

Quantity of flowers per lateral stem: 2 to 4.

Quantity of buds per lateral stem: 3 to 8.

Quantity of flowers and buds per plant: 100 to 150.

Persistent or self-cleaning: Persistent.

Fragrance: None.

Bud:

*Shape*.—Ovate.

*Length*.—1.5 cm.

*Diameter*.—1 cm.

*Color*.—RHS Yellow-Green 144A.

Flower:
*Type/form*.—Round whorl.
*Length*.—7.5 cm.
*Diameter*.—7.5 cm.
*Depth*.—4.5 cm.
*Aspect*.—Upright and outward.

Petals:
*Quantity*.—5 to 6.
*Arrangement*.—Whorl.
*Length*.—5.5 cm.
*Width*.—4.5 cm.
*Shape*.—Obovate.
*Apex*.—Obtuse.
*Base*.—Cuneate.
*Margin*.—Entire, with fine ciliate hairs near base only, colored RHS White 155A.
*Texture, upper and lower surfaces*.—Smooth and silky.
*Color*.—When opening, upper surface: RHS Purple 76A with Red-Purple 63A splotch near base, following a "feathering" pattern along veins; becoming White 155A at very base. When opening, lower surface: RHS Purple 76A. Fully opened, upper surface: RHS Purple 76A with Red-Purple 63A splotch near base, following a "feathering" pattern along veins; becoming White 155A at very base. Fully opened, lower surface: RHS Purple 76A.

Sepals:
*Appearance*.—Triangular shaped, fused at base, with additional linear structures arranged in a whorl beneath main sepals.
*Arrangement*.—Whorl.
*Quantity*.—5 to 6 main sepals with 6 to 9 additional linear extensions.
*Length*.—Main: 1 cm. Secondary: 2 cm.
*Width*.—Main: 6 mm. Secondary: 2 mm.
*Shape*.—Main: Triangular. Secondary: Linear.
*Margin*.—Entire.
*Apex*.—Acute.
*Base*.—Fused.
*Color*.—Upper side: RHS Yellow-Green 144A. Under side: RHS Yellow-Green 144A.
*Texture*.—Upper side: Smooth, lightly pubescent. Under side: Smooth.

Calyx:
*Shape*.—Collar-like.
*Length*.—1.5 cm.
*Width*.—1.75 cm.

Peduncle:
*Length*.—2.25 cm.
*Diameter*.—3 mm.
*Angle*.—15° to 45°.
*Strength*.—Good.
*Texture*.—Pubescent.
*Color*.—RHS Yellow-Green 144A.

REPRODUCTIVE ORGANS

Stamens:
*Number*.—About 75.
*Filament length*.—3 mm.
*Filament color*.—RHS White NN155A.

Anthers:
*Shape*.—Rounded.
*Length*.—1 mm.
*Color*.—RHS Yellow 4C.
*Pollen color*.—RHS Yellow 4D.
*Pollen amount*.—Abundant.

Pistil:
*Arrangement*.—Pistil fused, 5 protruding stigma from top.
*Number*.—1.
*Length*.—3.5 cm.
*Style*.—Length: 3.5 cm. Color: RHS White NN155A.
*Stigma*.—Shape: Peltate. Color: RHS White 155A. Ovary Color: RHS White NN155A.

OTHER CHARACTERISTICS

Seeds: Not observed.

Disease/pest resistance: Neither resistance nor susceptibility to normal diseases and pests of *Hibiscus syriacus* or *Hibiscus paramutabilis* have been observed.

Temperature tolerance: Low temperature tolerance to −31° C., high temperature tolerance to at least 38° C.

What is claimed is:

1. A new and distinct cultivar of *Hibiscus* plant named 'MINPAPAN1' as herein illustrated and described.

* * * * *